United States Patent
Choudhary et al.

(10) Patent No.: US 9,387,186 B2
(45) Date of Patent: Jul. 12, 2016

(54) THIOUREA DERIVATIVES

(71) Applicants: Muhammad Iqbal Choudhary, Karachi (PK); Saba Farooq, Karachi (PK); Khalid M. Khan, Karachi (PK); Farzana Naz, Karachi (PK); Atia-tul Wahab, Karachi (PK); Atta-ur Rahman, Karachi (PK)

(72) Inventors: Muhammad Iqbal Choudhary, Karachi (PK); Saba Farooq, Karachi (PK); Khalid M. Khan, Karachi (PK); Farzana Naz, Karachi (PK); Atia-tul Wahab, Karachi (PK); Atta-ur Rahman, Karachi (PK)

( * ) Notice: Subject to any disclaimer, the term of this patent is extended or adjusted under 35 U.S.C. 154(b) by 0 days.

(21) Appl. No.: 14/285,213

(22) Filed: May 22, 2014

(65) Prior Publication Data

US 2015/0335594 A1 Nov. 26, 2015

(51) Int. Cl.
| | | |
|---|---|---|
| *A61K 31/17* | (2006.01) | |
| *A61K 31/7036* | (2006.01) | |
| *A61K 31/165* | (2006.01) | |
| *A61K 31/496* | (2006.01) | |
| *A61K 31/7056* | (2006.01) | |
| *A61K 31/43* | (2006.01) | |
| *A61K 31/42* | (2006.01) | |

(52) U.S. Cl.
CPC .............. *A61K 31/17* (2013.01); *A61K 31/165* (2013.01); *A61K 31/42* (2013.01); *A61K 31/43* (2013.01); *A61K 31/496* (2013.01); *A61K 31/7036* (2013.01); *A61K 31/7056* (2013.01)

(58) Field of Classification Search
CPC . A61K 31/17; A61K 31/165; A61K 31/7056; A61K 31/42; A61K 31/7036; A61K 31/496; A61K 31/43
USPC ........... 514/25, 210.05, 253.08, 380, 40, 585, 514/587
See application file for complete search history.

(56) References Cited

U.S. PATENT DOCUMENTS

| | | | |
|---|---|---|---|
| 2006/0111302 A1* | 5/2006 | Romesberg | C07K 14/245 424/164.1 |
| 2015/0080580 A1* | 3/2015 | Rahman | C07D 213/75 546/305 |

OTHER PUBLICATIONS

Casely et al. AntibacterialS ynergismin Comprised of Halogenated Bisphenolasn d Substituted Systems Ureas. J. Soc. Cosmetic Chemists, 19:159-162, 1968.*
Suller et al. Antibiotic and biocide resistance in methicillin-resistant *Stuphylococcus aureus* and vancomycin-resistant enterococcus. journal of Hospital infection ( 1999) 43: 281-291.*

* cited by examiner

*Primary Examiner* — Clinton Brooks
*Assistant Examiner* — Yih-Horng Shiao
(74) *Attorney, Agent, or Firm* — Sarfaraz K. Niazi (57) ABSTRACT

Two thiourea derivatives N-(3-chlorophenyl)-N'-(3,4-difluorophenyl)thiourea and N-(3-chlorophenyl)-N-(3-methoxyphenyl)-thiourea are reported as treatment of multidrug resistance infections from *Staphylococcus aureus*.

10 Claims, 9 Drawing Sheets

THIOUREA DERIVATIVES

BACKGROUND OF THE INVENTION

Due to the beneficial effects of thiourea derivatives in many therapeutic areas such as anti-cancer, anti-bacterial, anti-fungal, anti-malarial and anti-tuberculosis, these compounds have acquired major action as a new drug agents. (Nur Illane Mohamad Halim et. al., 2011). Carbmides and carbamates derivatives have also been reported to possess significant anti-microbial, cytotoxicity, and anti-inflammatory activities (Irfan A. Mohammed et. al. 2010).

Although there are many antimicrobials and chemotherapeutics agents already available for the treatment of a wide range of infectious diseases, the emerging antimicrobial resistance demand the discovery of a new class of anti-bacterial agents. The antimicrobial resistance is considered a serious threat for health and it requires an alternative approach to its management. Based on this need, new drugs have been developed for the control of bacterial resistance and, some urea and thiourea derivatives are among them (P. Umadevi et al., 2012).

Thiourea derivatives have attracted the attention of several research groups due to their potential in medicinal chemistry. Moreover, it has been previously reported that by the introduction of halogen atoms to the pharmacophore structure of thiourea, the antimicrobial activity can be enhanced (Yildiz GUlkok et. al., 2011).

The syntheses and evaluation of antibacterial activity of urea and several of its derivatives have been the subject of numerous investigations (Figueroa V. L. et. al., 2008).

The instant invention reports two new derivatives active against multiple drug resistant (MDR) bacteria *Staphylococcus aureus*, which cause many life threatening and common infections.

BRIEF SUMMARY OF THE INVENTION

The present invention relates to the treatment of MDR bacteria, such as drug-resistant *Staphylococcus aureus*, with thiourea derivatives capable of inhibiting growth.

According to another of its aspects, the treatment methods of the invention relate to pharmaceutical compositions comprising, as active principle, compound I or II according to Table 1, for the treatment and/or prevention of the pathologies caused by *Staphylococcus aureus*. These pharmaceutical compositions contain an effective dose of the compound according to the invention, as well as at least one pharmaceutically effective excipient, diluent, or adjuvant.

Said excipients are selected, according to the pharmaceutical form and the desired route of administration, from the usual excipients that are known to a person skilled in the art.

In the pharmaceutical compositions used in the treatment of the present invention for oral, sublingual, subcutaneous, intramuscular, intravenous, topical, local, intratracheal, nasal, transdermal or rectal administration, the compound can be administered in dosage units, mixed with conventional pharmaceutical excipients, to animals and to humans for the prevention or for the treatment of the disorders or diseases mentioned above.

Appropriate dosage units comprise forms for the oral route such as tablets, soft or hard capsules, powders, granules and oral solutions or suspensions; sublingual, buccal, intratracheal, intraocular, nasal, and inhalation forms of administration; topical, transdermal, subcutaneous, intramuscular or intravenous forms of administration; rectal forms of administration, and implants. For topical application, compounds according to the invention can be used in creams, gels, ointments or lotions.

The composition of the invention can be administered by the most suitable route and at a dose that depends in particular on the nature of the infection, on the type of host in question, on the host's age, weight and general condition, on concomitant treatments being received, as well as on the host's response to the treatment and to the therapeutic rationale.

BRIEF DESCRIPTION OF THE SEVERAL VIEWS OF THE DRAWING

FIGS. 4A and 4B depict the reversal of multidrug resistance in both EMRSA-16 and -17 by compounds I and II.

FIGS. 5A and 5B depict compound-induced damage through generation of Reactive Oxygen Species ($O_2^-$) in EMRSA-16 and -17 after the treatment with I and II by using the CL assay with the lucigenin as a detector.

DETAILED DESCRIPTION OF THE INVENTION

The present invention is valuable as an anti-microbial drug against drug-resistant strains of *Staphylococcus aureus* and the treatment of infections caused by these drug resistant strains.

The emerging gap among the rising incidence of diseases which are caused by MDR bacterial strains and the rapid reduction in the development of novel drugs is now frightening and pushing us back into pre-antibiotic age. Therefore, there is a critical necessity to develop novel antimicrobials to treat latent MDR infections. In the instant invention, we report the inhibitory and mechanistic effects of thiourea derivatives against MDR bacteria *Staphylococcus aureus*. We screened a number of thiourea derivatives for their possible effect as an antibiotic against bacteria. Four resistant strains of *S. aureus* were used, a resistant strain which was isolated from a local hospital, and standard laboratory strains from the NCTC culture collection included (EMRSA-17, EMRSA-16, and MRSA-252). These active and reproducible inhibitors have the potential to possibly block the efflux pumps, alters the membrane potential, revert the multi-drug resistance, and induce the ROS production in MDR *Staph. aureus*.

Example 1

High Throughput Screening Assay (MABA) Against MDR *S. aureus*

Inocula Preparation:
In growth medium (Muller Hinton broth), the pure isolated colonies were inoculated and incubated at 37° C. for 20-24 hours. After 20-24 hours, the turbidity was checked and adjusted to 0.5 McFarland standards.

Assay Protocol:

For this assay, the stock solutions of 1 mg/mL concentration of compounds (I and II) were made by using DMSO. 96-Wells sterile, flat bottom micro titer plates were used with proper labeling, 20 µg/mL of both compounds were added in first wells and made two fold serial dilutions by using sterile broth. The cells suspensions (conc. $5\times10^5$) were then added in each wells, finally the volume was made up with broth up to 200 µL in each well. The plate was sealed and incubated at 37° C. for 20-24 hours. Experiments were carried out in triplicate manner. After incubation of 20-24 hours, Alamar Blue Dye was added (10%) to the culture volume and kept the plates on shaking incubator at 37° C. for 3 to 4 hours. Change in color was then assessed visually and qualitatively. Quantitative analysis was recorded by taking absorbance at 570 and 600 nm by a spectrophotometer.

The above mentioned protocol was followed by the method reported by Sarkar et al., (2007) with slight modifications.

Percentage reduction and inhibition of Alamar blue dye was calculated by using the following formulas:

1. Percent reduction:

$$\frac{(\varepsilon ox)\lambda 2 A\lambda 1 - (\varepsilon ox)\lambda 1 A\lambda 2}{(\varepsilon red)\lambda 1 A'\lambda 2 - (\varepsilon red)\lambda 2 A'\lambda 1} \times 100$$

Where,
$\varepsilon ox$=molar extinction coefficient of Alamar blue oxidized form (blue)
$\varepsilon red$=molar extinction coefficient of Alamar blue reduced form (pink)
A=absorbance of test wells
A'=absorbance of negative control well
$\lambda 1$=570 nm
$\lambda 2$=600 nm Here control wells contain only media plus Alamar Blue, while the test wells contain both Alamar Blue with the test compounds.

2. Percent difference in reduction:

$$\frac{(\varepsilon ox)\lambda 2 A\lambda 1 - (\varepsilon ox)\lambda 1 A\lambda 2 \text{ of test agent dilution}}{(\varepsilon ox)\lambda 1 A°\lambda 2 - (\varepsilon ox)\lambda 2 A°\lambda 1 \text{ of untreated positive growth control}} \times 100$$

Where,
$\varepsilon ox$=molar extinction coefficient of Alamar blue oxidized form (blue)
A=absorbance of test wells
A°=absorbance of positive growth control well
$\lambda 1$=570 nm
$\lambda 2$=600 nm Here control wells contain cells+media+Alamar Blue, while the test wells contain both Alamar Blue with the test compounds+cells (The percent inhibitions are available in Table 1).

TABLE 1

Results of High throughput Screening Assay (MABA) against MDR *S. aureus*.

| Compounds | IUPAC Name | Structure | % Inhibition 20 µg/mL EMRSA-17 | % Inhibition 20 µg/mL Clinical Isolates | % Inhibition 20 µg/mL EMRSA-16 | % Inhibition 20 µg/mL MRSA 252 |
|---|---|---|---|---|---|---|
| I | N-(3-Chlorophenyl)-N'-(3,4-difluorophenyl) thiourea | [structure] | 71.522 | 20.00 | 48.438 | 24.457 |
| II | N-(3-Chlorophenyl)-N-(3methoxyphenyl) thiourea | [structure] | 82.632 | 19.600 | 50.053 | 14.837 |
| Urea | Carbamide, carbonyl diamide, carbonyldiamine, Diaminomethanal | [structure] | No Inhibition | No Inhibition | No Inhibition | No Inhibition |
| Thiourea | Thiocarbamide | [structure] | No Inhibition | No Inhibition | No Inhibition | No Inhibition |

Results of High throughput screening assay (MABA) against EMRSA-16 and -17: The results of both quantitative and qualitative analysis showed that thiourea derivative I and II possess activity against a variety of drug resistant *Staphylococcus aureus* strains. Results summarized in Table 1 showed that all strains were resistant to both urea and thiourea, while compounds I and II were active against EMRSA-16 and -17 at the concentration of 20 µg/mL.

Example 2

Effect of I and II on the Membrane Potential and Integrity (ΔΨ) of EMRSA-16 AND-17

Compound Treatment:
20 µg/mL of compounds I and II were tested against $5\times10^5$ multidrug resistant *S. aureus* cells and incubated for 20-24 hours, while cells without compounds were taken as a control.

Cell Staining:
Stock solution (1 mg/mL) for the membrane potential probe $DiBAC_4(3)$ was made in absolute ethanol and stored at −20° C. 1 mL of exponentially growing *S. aureus* were taken from broth cultures and centrifuged at 11,000 rpm for 2 mins Supernatant was discarded and cells pallets were dissolved in 4 mL of filtered phosphate-buffered saline (PBS). Final 10 µg/mL conc. of fluorogenic substrates $DiBAC_4$ were adjusted in 4 mL volume. The stained cell suspension was incubated at 37° C. for 30 min. Before flow cytometric analysis, cells were washed in PBS buffer by centrifugation.

The above mentioned protocol was adapted from the procedures of Jepras et al. (1997) with slight modifications.

Flow Cytometry Data Acquisition:
Assays were performed by using Becton Dickinson FACSCaliber™ flow cytometer (USA). A total of 50,000 cells were counted by using Cell Quest software (BD) for data acquisition and analysis. $DiBAC_4(3)$ was detected as green fluorescence in the channel FL1 (Veal et al., 2000).

Results of membrane potential studies against EMRSA-16 and -17. In membrane potential assay, by using Dot, Contour, and 3D plots (FIGS. 1A and 1B), light scattering properties and $DiBAC_4(3)$ green fluorescence were measured. (A1 and B1) were the control dot plots, while (A2 and B2) were the treated ones, indicated that after the treatment with compounds, the cell populations were moved towards the green fluorescence (FL-1). This movement of cells from the confined and fixed place to FL-1 region showed a clear discrimination between the control and treated cells. Compound treatment caused the rapid and increased fluorescence which was due to the entry of dye inside the cells, showing the membrane damage and alteration. Similarly in A4 and B4, shift in treated cells were observed with increase fluorescence (frequency events) in contour plots, while in controlled one the well-defined pattern was observed.

Figure 1A:
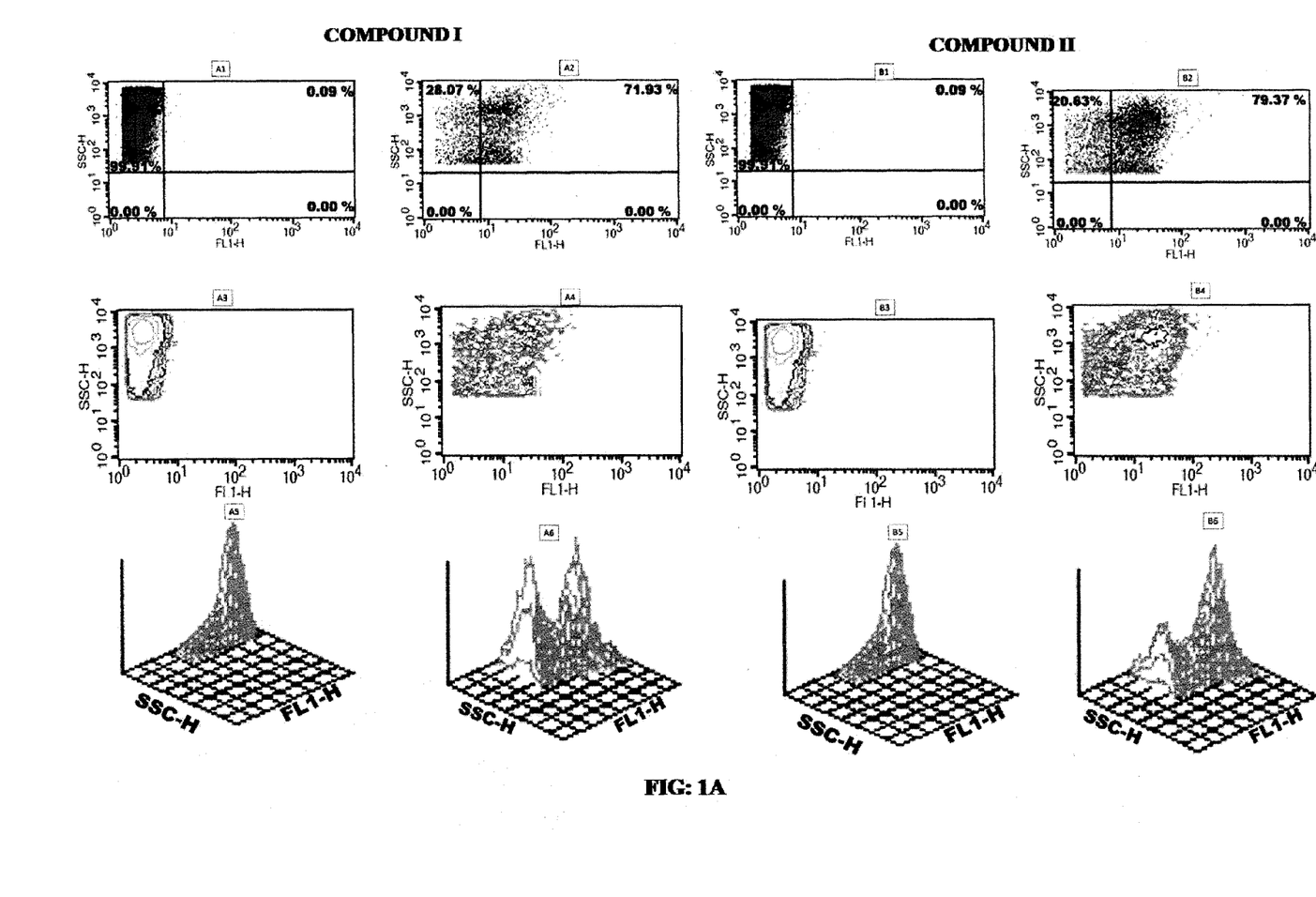
FIGS. 1A and 1B depict the effect of compounds I and II on the membrane potential and integrity ($\Delta\Psi$) of MDR *S. aureus*. Dot plots (A1, A2, B1 and B2), Contour plots (A3, A4, B3 and B4) and 3D plots (A5, A6, B5 and B6) represents the FL1 log DiBAC4(3) fluorescence versus side scatter (SSC). By using both EMRSA-16 and -17, the plots (A1, A3, A5 and B1, B3 and B5) taken after 20 hrs. of growth without any treatment, while with the treatment of 20 µg/mL conc. of compounds I and II (A2, A4, A6, and B2, B4 and B6).
Figure 1B:
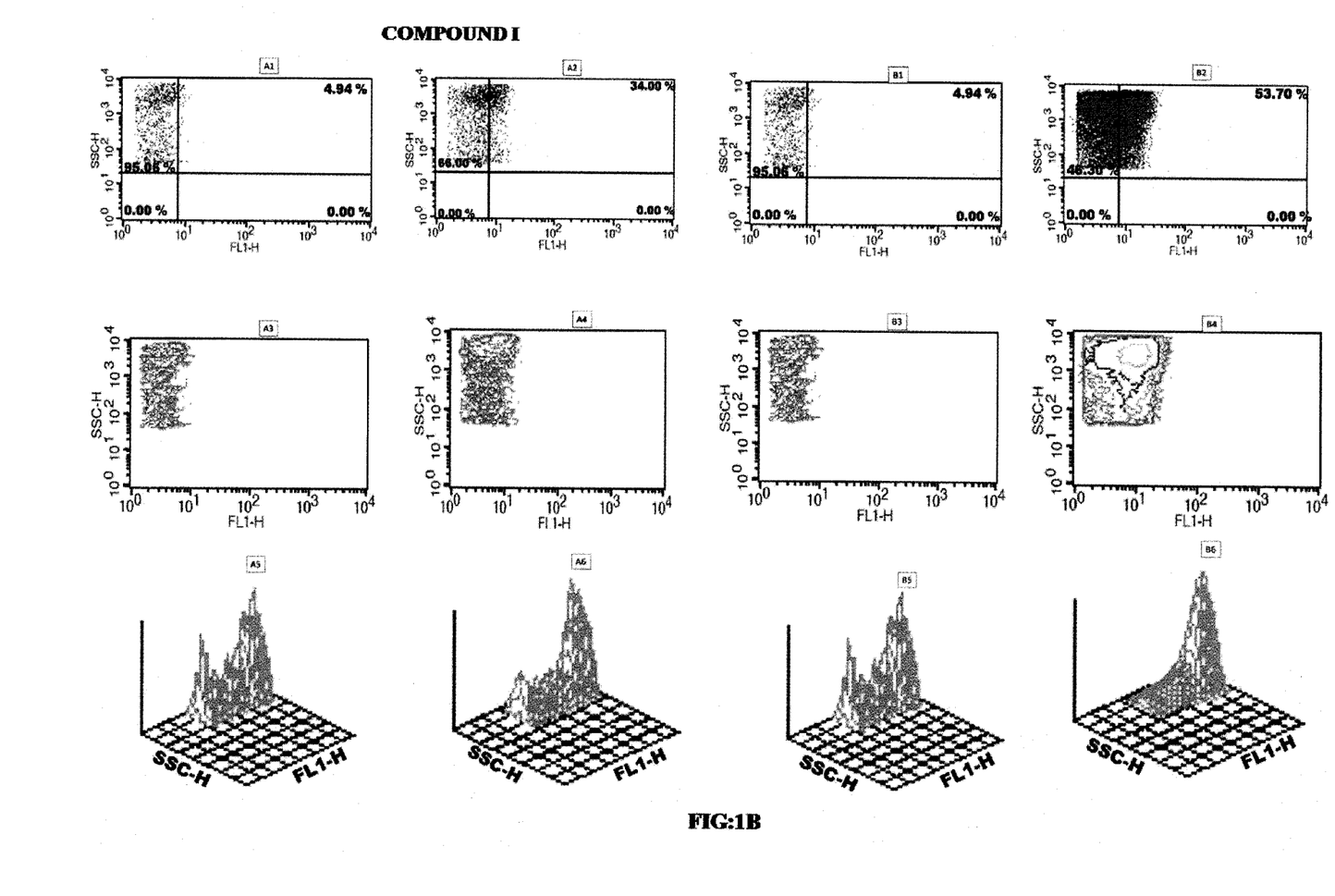
Figure 2A:
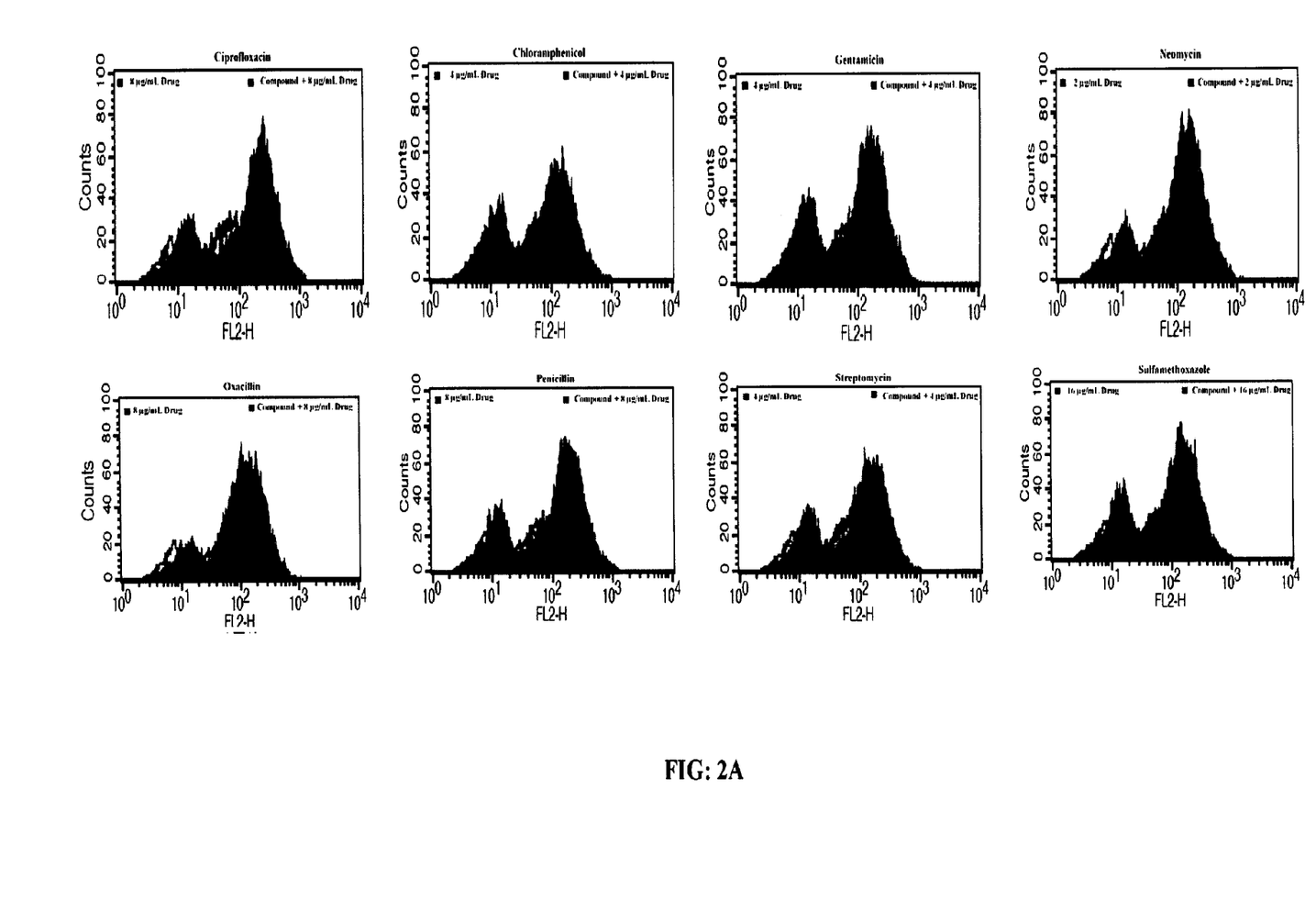
FIGS. 2A, 2B, 3A and 3B depict increased sensitivity of MDR bacteria (EMRSA-16 and 17) to antibiotics (drugs) by blocking the MDR Efflux Pumps. Flow cytometery histogram showing EtBr accumulation in both MDR strains. Treated with antibiotic and thiourea derivative alone and in combinations of different class of antibiotics.
Figure 2B:
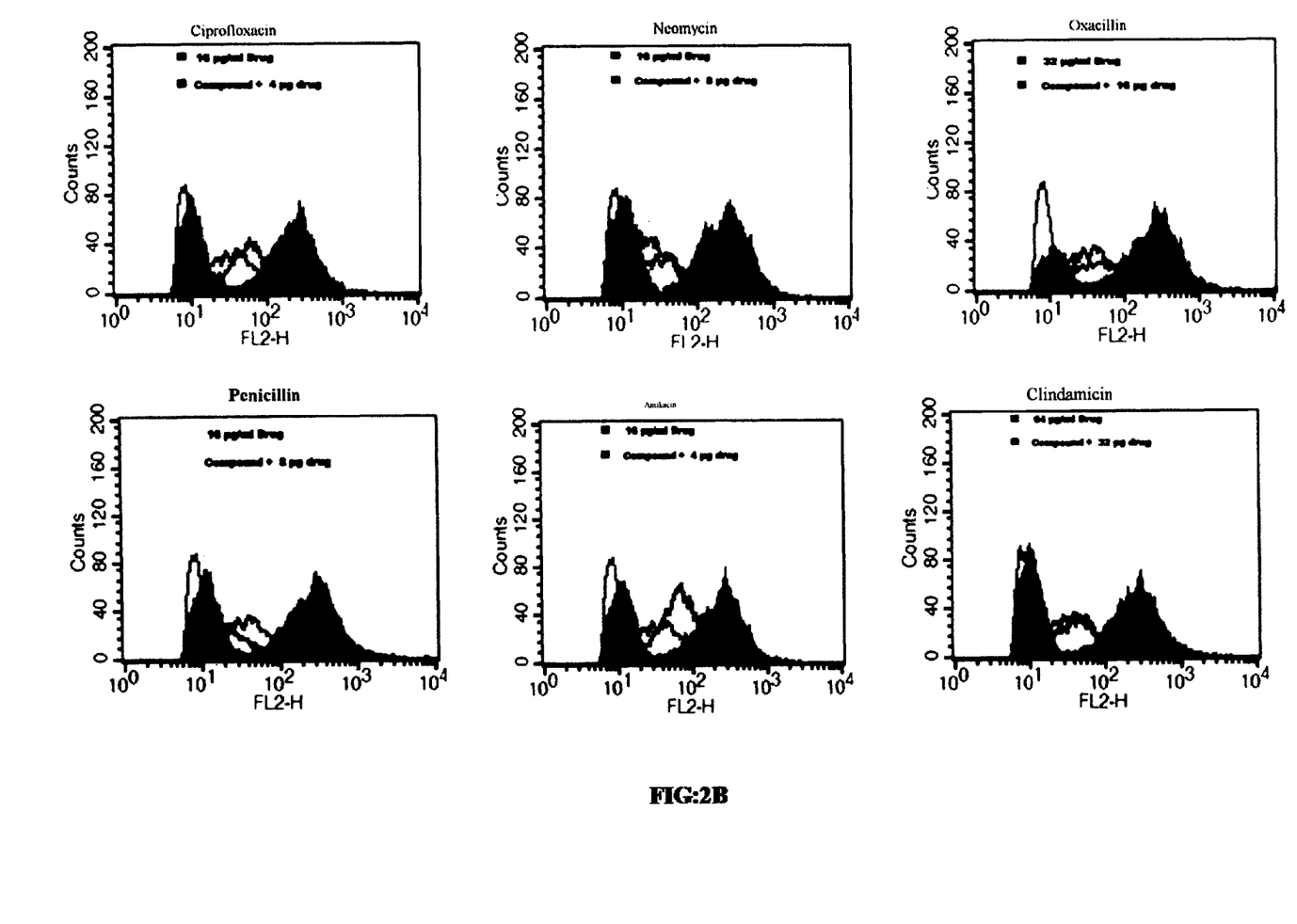
Figure 3A:
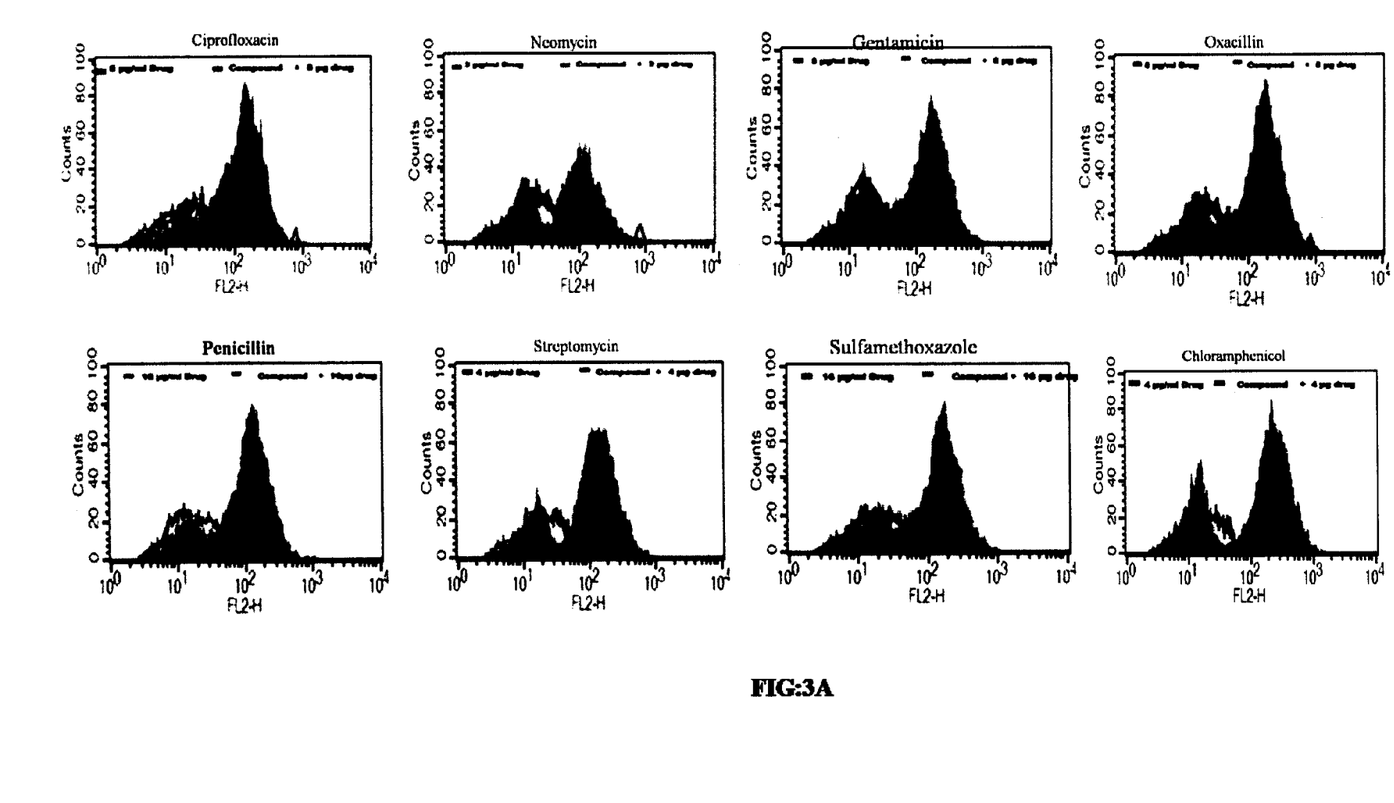
Figure 3B:
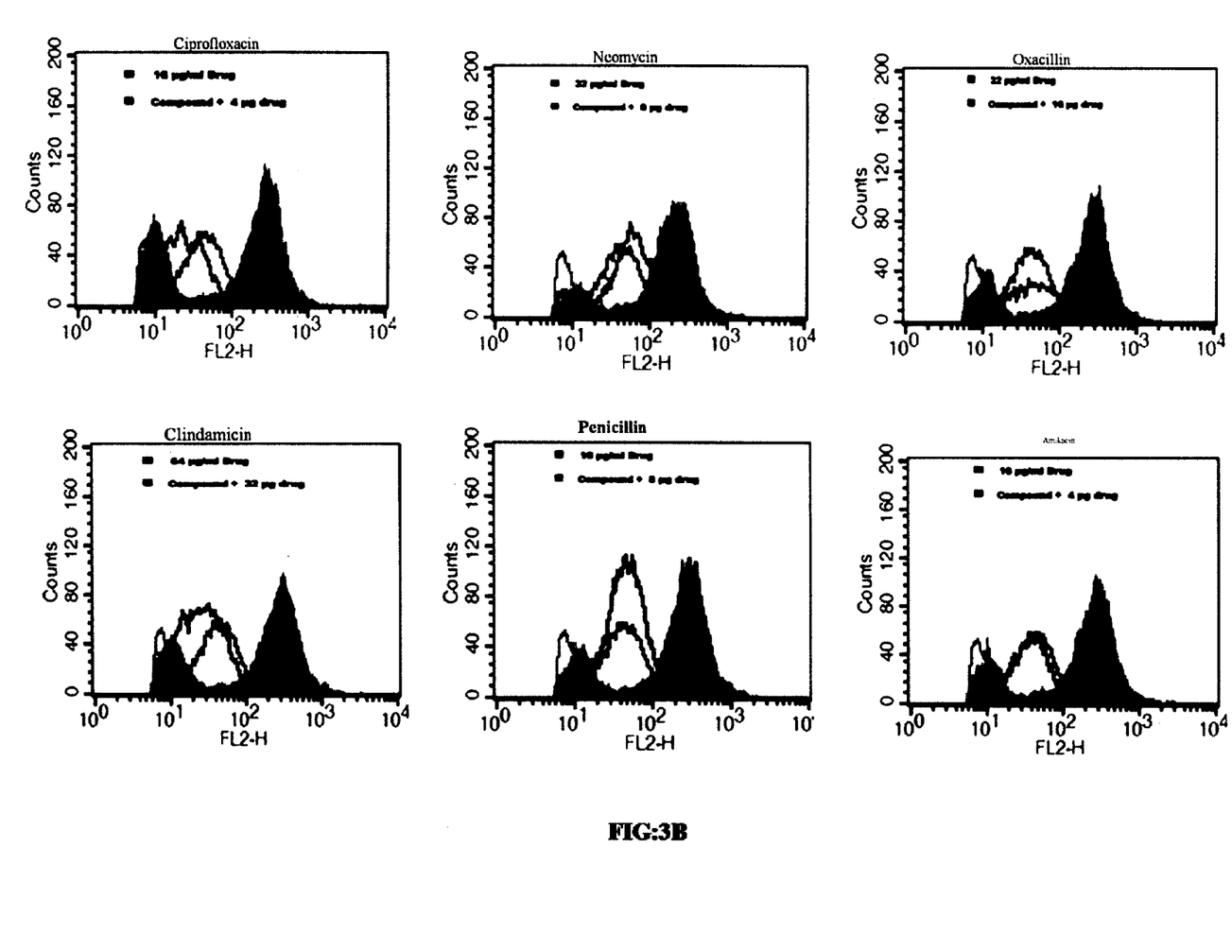

3D Plots were shown the same results; the compound caused the dynamic changes in peak pattern. In plots A6 and B6, due to the presence of compounds I and II changes in membrane potential were observed and the huge cellular population was shifted in rapid regular pattern towards the area of increasing fluorescence mainly due to the binding of dye inside the cellular content.

Studies on membrane potential or integrity indicated that when cells were treated with compounds I and II, there was a quick and fast uptake of dye $DiBAC_4(3)$ inside the cells representing the compound induced cellular alteration, depolarization and the disruption of cytoplasmic membrane. While antibiotics alone had the least effect on cellular potential i.e., neither caused depolarization nor increased or altered permeability even at high concentrations. The green fluorescent dye $DiBAC_4(3)$ has the ability to accumulate inside the injured/depolarized cells by binding to intracellular proteins and membranes. The loss of membrane potential was measured with the green fluorescent bis-oxonol $DiBAC_4(3)$ FL1, 520 nm (Berney, et al., 2006).

Example 3

Reversal of Multi-Drug Resistance by Compounds (I and II)

Assay Protocol:
Fixed concentration of compounds I and II and increasing concentration of antibiotics (drugs) were made in 96-well plates. $5\times10^5$ multidrug resistant *S. aureus* cells were added in each well and incubated for 20-24 hours. No test compounds and antibiotics were present in control wells Inhibition and growth were noted both visually and by using the dye Alamar blue.

FIC of Antibiotic *a* ($FIC_a$)=MIC of Antibiotic *a* in combination/MIC of Antibiotic *a* alone FIC of Compound *b* ($FIC_b$)=MIC of Compound *b* in combination/MIC of Compound *b* alone The sum of Fractional Inhibitory Concentration ($FIC_s$) index of ($FIC_a$)+($FIC_b$)=($FIC_s$). Fractional inhibitory concentrations were calculated by the above cited formula. (The FIC values of compounds I and II are available (FIGS. 4A and 4B). Protocol of Chung et al. (2011), with slight modifications, was followed for above discussed reversal resistance assay.

Results of Reversal of Multidrug Resistance by Compounds I and II in EMRSA-16 and -17: The MIC of compound I was found to be 28 µg/mL while the MIC of compound II was found to be 25 µg/mL for EMRSA-17. Similarly, the MIC of compounds I was found to be 52 µg/mL while the MICs of compound II were found to be 52 µg/mL for EMRSA-16. The highly resistant organisms are efficiently use their resistance mechanisms, so the MICs of the tested drugs were found to be much higher than both the compounds I and II. For EMRSA-17, when the combination of compounds I and II were used, the MICs become dramatically reduced up to 2 to 16 µg/mL, while alone the MICs of antibiotics amikacin, ciprofloxacin, clindamycin, gentamicin, neomycin, oxacillin, penicillin, and sulfamethoxazole were found to be 256, 1024, 4096, 1024, 512, 2048, 1024, and 2084 µg/mL, respectively. This dramatic lowering of MIC (over 1000 fold) in combination of above mentioned drugs showed substantial synergistic action, while sulfamethoxazole showed indifference effect with both compounds. Clindamycin also showed indifference effect with compound I only.

Similarly the MICs of amikacin, chloramphenicol, ciprofloxacin, clindamycin, gentamicin, neomycin, oxacillin, and penicillin, in combination of compounds were also dramatically reduced to 4, 16, 4, 32, 8, 8, 16, and 8 µg/mL, respectively, against EMRSA-16. In most of the combinations, strong synergistic activities were observed, only clindamycin showed a partial synergistic activity with both the compounds I and II.

For the production of strong synergism and the expansion of antibacterial spectrum, different combinations of compounds and drugs are in common usage, for example augmentin, which is the combination of two drugs (amoxicillin and clavulanate).

The FIC index is the most frequently used method to determine the interaction between compounds and drugs. Fractional Inhibitory Concentration Index (FICI) is the sum of FICs of drugs+test compounds. Briefly, the different combinations of test compound and drugs (antibiotics) exerts different effects includes; synergistic or additive effects on the growth of bacteria, as compared to single antimicrobial agent (Amber Farooqui et al., 2008).

Sato and colleagues (2004) investigated the effect 6, 7-dihydroxyflavone as a weak antibacterial against MRSA, but at sub-MIC concentration it elevated the susceptibility to β-lactam antibiotics (Bakar et al. 2012).

In the instant invention, we observed that even at lowest concentrations, the combinations of drugs and compounds were responsible for causing the dramatic increase in the sensitivity of cells and making the MDR cells again susceptible for previously failed antibiotics. While the drugs (alone) were inactive or poorly active at highest dosage. Therefore, in different combinations of compounds with the antibiotics drugs, the MICs were now reduced up to thousand folds, while MICs of drugs (alone) were exceedingly high such as 1000 µg/mL or more.

Example 4

Increased Sensitivity of MDR Bacteria to Drugs Through Inhibition of the MDR Efflux Pumps Assay Protocol: Different combinations of compounds I and II with antibiotics, and antibiotic alone, were made and incubated with bacterial cells for 3 hrs. After incubation cells were stained with ethidium bromide. Both the control and treated cells were centrifuged for 3 mins at 13,000 rpm. The pallet was washed with PBS. Negative control was free from ethidium bromide (EtBr), while positive control contains (EtBr). By using FL2 channel, FACS analyses were carried out. Protocol of Kalle et al. (2009) was employed with some modifications.

Flow cytometry data acquisition: For data acquisition and analysis Cell Quest software (BD) were used. A total number of 50,000 cells were counted. EtBr fluorescence was detected through (FL-2 channel).

Results of Inhibition of Efflux pump by Compounds I and II in EMRSA-16 and -17. Ethidium bromide was used in the efflux pump inhibition studies and was conducted through FACS, it binds or intercalates with DNA. Data was taken between the FL-2 channel and cell counts. Control cells (labelled, and unlabeled), cells with drugs (antibiotics alone) and cells with combinations of drugs+compounds were shown in (FIGS. 2A, 2B, 3A and 3B). In living cells, by using their efflux system, the multidrug resistant organism actively efflux or exclude out the (EtBr) dye, which enters only in dead, damaging or injured cells.

Normal/untreated control bacterial cell populations were confined in a starting region of histograms, while the antibiotic treated population were also present on the same or near the control regions. Cells with the higher concentrations of antibiotics were found to be all alive, indicating the overexpressed efflux system.

When cells were treated with the combination of compounds and antibiotic drugs, alteration or inhibition of efflux pumps, were observed. Bacteria were not further able to efflux out the EtBr, whereas physical alterations in cell wall was also observed. Cellular granularities, as well as complexity, were affected/changed and prominent peaks shifting was observed, along with the rapid increase in the intensity of red fluorescence inside the cells.

Different combinations of antibiotics and the compounds I and II, caused a decrease in the efflux activity, which was directly associated with a significant increase in the amount of cell-based fluorescence. This clearly indicated that compounds I and II have the excellent capacity to inhibit the bacterial efflux pump mechanism.

Combinational therapy by using the efflux pump inhibitors (test compounds) and antibiotics has been shown to increase the intracellular concentration of antibiotics, thereby reversing the resistance (Kalle and Rizvi et al., 2011).

Therefore, by using the EtBr efflux assay, it was concluded that compounds I and II facilitate the accumulation of antibiotics drug in the resistant strains of *S. aureus*. This indicated the therapeutic potential of both compounds to significantly reverse the multidrug resistance in bacteria and to increase the sensitivity of bacteria towards existing antibiotics, even at very low concentrations.

Example 5

Compound Induced Damage Through Production Reactive Oxygen Species ($O_2^-$) in MDR *Staphylococcus aureus* in Lucigenin CL Assay Assay Protocol: $5 \times 10^5$ Cells were incubated with the different concentrations of compounds (25, 50 and 100. µg/mL), leucigenin and filtered phosphate buffer saline. For the triggering of reaction, DMSO was added to the each well at the time of RLU determination. No test compounds were added in positive control but it contained DMSO, while no test compound and DMSO were added in negative control. Chemiluminescence (CL) was determined at room temperature by luminometer. The light emission results were measured in relative light unit (RLU). Protocol of above discussed protocol was followed by the method of Albesa et al (2002) with slight modifications.

Results of Compound-Induced Damage through Production of Reactive Oxygen Species ($O_2^-$) in MDR *Staphylococcus aureus* in Lucigenin CL Assay In Lucigenin CL assay, after the treatment of EMRSA-16 and -17 with compounds 1 and II, more production of $O_2^-$ was observed (FIG. 6 and). The production and liberation of intracellular $O_2^-$ was not detected in positive and negative controls, even in the presence of DMSO which acted as activator. It is observed that compound-induces the production of intracellular $O_2^-$, which is one of the main reasons for causing damage to the resistant cells. Very minute quantity of $O_2^-$ in the cells can cause cell damage.

In a variety of bacterial strains, both gram positive and gram negative, the generation of lethal hydroxyl radicals were produced by many classes of antibiotics (Dwyer et al., 2009).

During this study, the generation of $O_2^-$ in MDR cells were detected after the treatment of compounds I and II. This $O_2^-$ were damaged the cell effectively by direct attack. Main reason of the cellular death and alteration of cell physiology is the production of ROS ($O_2^-$). A higher $O_2^-$ level was observed in treated cells with both the thiourea derivatives in a dose dependent manner which indicated the bacterial cell damaged by the formation of ROS.

What is claimed is:

1. A method of inhibiting a multidrug resistant strain of *Staphylococcus aureus* comprising administering a suitable amount from 20 µg/ml to 100 µg/ml of N-(3-Chlorophenyl)-N'-(3, 4-difluorophenyl)thiourea to a mammal in need thereof.

2. A method of inhibiting a multidrug resistant strain of *Staphylococcus aureus* comprising administering a suitable amount from 20 µg/ml to 100 µg/ml of N-(3-Chlorophenyl)-N-(3-methoxyphenyl)thiourea to a mammal in need thereof.

3. A method of treating a disease or infection in a mammal caused by a multidrug resistant strain of *Staphylococcus aureus* comprising administering a suitable amount from 20 µg/ml to 100 µg/ml of N-(3-Chlorophenyl)-N'-(3, 4-difluorophenyl)thiourea to the mammal in need thereof.

4. A method of treating a disease or infection in a mammal caused by a multidrug resistant strain of *Staphylococcus aureus* comprising administering a suitable amount from 20 µg/ml to 100 µg/ml of N-(3-Chlorophenyl)-N-(3-methoxyphenyl)thiourea to the mammal in need thereof.

5. A method of inhibiting bacterial cell efflux pumps by inducing reactive oxygen species (ROS) in a multidrug resistant strain of *Staphylococcus aureus* comprising administering a suitable amount from 20 µg/ml to 100 µg/ml of N-(3-Chlorophenyl)-N'-(3, 4-difluorophenyl)thiourea to a mammal in need thereof.

6. A method of inhibiting bacterial cell efflux pumps by inducing reactive oxygen species (ROS) in a multidrug resistant strain of *Staphylococcus aureus* comprising administering a suitable amount from 20 µg/ml to 100 µg/ml of N-(3-Chlorophenyl)-N-(3-methoxyphenyl)thiourea to a mammal in need thereof.

7. The method of claim 3 further comprising administering an antibiotic chosen from the group consisting of amikacin, chloramphenicol, ciprofloxacin, clindamycin, gentamicin, neomycin, oxacillin, penicillin, and sulfamethoxazole.

8. The method of claim 4 further comprising administering an antibiotic chosen from the group consisting of amikacin, chloramphenicol, ciprofloxacin, clindamycin, gentamicin, neomycin, oxacillin, penicillin, sulfamethoxazole.

9. The method of claim 3, wherein the thiourea further comprises a pharmaceutically acceptable excipient, adjuvant, carrier or diluent.

10. The method of claim 4, wherein the thiourea further comprises a pharmaceutically acceptable excipient, adjuvant, carrier or diluent.

* * * * *